United States Patent
Ho et al.

(10) Patent No.: US 12,161,682 B2
(45) Date of Patent: *Dec. 10, 2024

(54) TOPICAL COMPOSITION AND METHOD OF IMPROVING SKIN DISEASES AND DERMATITIS USING THE SAME

(71) Applicant: GLAC BIOTECH CO., LTD., Tainan (TW)

(72) Inventors: Hsieh-Hsun Ho, Tainan (TW); Yi-Wei Kuo, Tainan (TW); Ching-Wei Chen, Tainan (TW); Yu-Fen Huang, Tainan (TW); Jia-Hung Lin, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/205,127

(22) Filed: Mar. 18, 2021

(65) Prior Publication Data
US 2021/0401907 A1    Dec. 30, 2021

(30) Foreign Application Priority Data

Jun. 30, 2020   (TW) .................. 109122130

(51) Int. Cl.
*A61K 35/747*      (2015.01)
*A61K 8/99*        (2017.01)
(Continued)

(52) U.S. Cl.
CPC .......... *A61K 35/747* (2013.01); *A61K 8/99* (2013.01); *A61K 9/0014* (2013.01);
(Continued)

(58) Field of Classification Search
CPC ...... A61K 35/747; A61K 8/99; A61K 9/0014; A61K 35/745; A61K 47/42; A61K 47/46;
(Continued)

(56) References Cited

U.S. PATENT DOCUMENTS

| 2003/0049231 A1 | 3/2003 | Baur et al. |
| 2005/0089499 A1* | 4/2005 | Moussou ............ A61Q 19/005 424/773 |

(Continued)

FOREIGN PATENT DOCUMENTS

| CN | 102835657 A | 12/2012 |
| CN | 104644840 A | 5/2015 |

(Continued)

OTHER PUBLICATIONS

Masco L, Ventura M, Zink R, Huys G, Swings J. Reclassification of Bifidobacterium animalis as *Bifidobacterium animalis* subsp. *animalis* subsp. nov. and *Bifidobacterium lactis* as *Bifidobacterium animalis* subsp. *lactis* subsp. nov. Int J Syst Evol Microbiol. Jul. 2004;54(Pt 4):1137-1143. (Year: 2004).*

(Continued)

*Primary Examiner* — Thomas J. Visone
(74) *Attorney, Agent, or Firm* — Joseph C. Zucchero; Carolyn S. Elmore; Elmore Patent Law Group, P.C.

(57) ABSTRACT

The present invention provides a topical composition having a fermented product of lactic acid bacteria synbiotics as an active ingredient. The fermented product of lactic acid bacteria synbiotics is obtained by performing a fermenting step with lactic acid bacteria and a deactivating step on a fermenting substrate. The lactic acid bacteria are consisting of *Lactobacillus salivarius* subsp. *salicinius* AP-32, *Bifidobacterium animalis* subsp. *lactis* CP-9 and *Lactobacillus acidophilus* TYCA06. The fermenting substrate includes animal protein, plant protein and/or plant extracts. The aforementioned fermented product of lactic acid bacteria synbiotics can effectively inhibit the growth of *Staphylococcus aureus* and/or *Propionibacterium acnes*, and can be used in the topical composition.

7 Claims, 11 Drawing Sheets

(51) Int. Cl.
  *A61K 9/00*    (2006.01)
  *A61K 35/745*  (2015.01)
  *A61K 47/42*   (2017.01)
  *A61K 47/46*   (2006.01)
  *A61P 17/00*   (2006.01)
  *A61P 17/10*   (2006.01)
  *A61Q 19/00*   (2006.01)
  *A61K 35/00*   (2006.01)

(52) U.S. Cl.
  CPC ............ *A61K 35/745* (2013.01); *A61K 47/42* (2013.01); *A61K 47/46* (2013.01); *A61P 17/00* (2018.01); *A61P 17/10* (2018.01); *A61Q 19/007* (2013.01); *A61K 2035/115* (2013.01)

(58) Field of Classification Search
  CPC .. A61K 2035/115; A61K 36/23; A61K 36/28; A61K 36/282; A61K 36/48; A61K 36/82; A61K 8/64; A61K 8/986; A61K 38/011; A61K 2800/85; A61P 17/00; A61P 17/10; A61Q 19/007; A61Q 19/00
  See application file for complete search history.

(56) References Cited

U.S. PATENT DOCUMENTS

2009/0232785 A1* 9/2009 Breton .............. A61K 36/738
                                                    424/93.46
2017/0119827 A1* 5/2017 Kovarik ............. A61K 31/58

FOREIGN PATENT DOCUMENTS

| EP | 2704704 A1 * | 3/2014 | ........... A61K 31/205 |
| JP | 2014043397 A | 3/2014 | |
| KR | 20190023691 * | 3/2019 | |
| KR | 20190023691 A | 3/2019 | |
| WO | 0228402 A1 | 4/2002 | |

OTHER PUBLICATIONS

Katsuyoshi Chiba, Development of functional cosmetic ingredients using lactic acid bacteria in Japan, Japanese Journal of Lactic Acid Bacteria, 2007, vol. 18, Issue 3, pp. 105-112 (Year: 2007).*

Kang et al. Isolation and Identification of Lactic Acid Bacteria Inhibiting the Proliferation of Propionibacterium acnes and Staphylococcus epidermidis. Journal of Bacteriology and Virology 2009. vol. 39, No. 1 p. 11-19 (Year: 2009).*

Jeong et al. Probiotic Lactic Acid Bacteria and Skin Health. Critical Reviews in Food Science and Nutrition, 56:2331-2337 (Year: 2016).*

Sivamaruthi et al. Probiotic based therapy for atopic dermatitis: Outcomes of clinical studies. Asian Pacific Journal of Tropical Biomedicine 2018; 8(6): 328-332. (Year: 2018).*

Rusu et al. Probiotics in Atopic Dermatitis. Experimental and Therapeutic Medicine 18: 926-931, 2019. (Year: 2019).*

Hsieh et al., New Microbiol., 36:167-179 (2013) (Year: 2013).*

Mottin, V. et al., "An Approach on the Potential Use of Probiotics in the Treatment of Skin Conditions: Acne and Atopic Dermatitis", Int. J. Derm. doi: 10.1111/ijd.13972, 2018, 1-8.

Taverniti, V. et al., "The Immunomodulatory Properties of Probiotic Microorganisms Beyond Their Viability (Ghost Probiotics: Proposal of Paraprobiotic Concept)", Genes Nutr., vol. 6, DOI 10.1007/s12263-011-0218-x, Apr. 16, 2011, 261-274.

Wu, J. et al., "Effects of Probiotics on Skin Health and Its Mechanisms", Ind. Microbio., vol. 48, No. 5, doi: 10.3969 /j. issn.1001-6678.2018.05.003, Oct. 2018, 13-18.

* cited by examiner

| Strain | Preparation example 11 AP-32+CP-9+TYCA06 | | | | Comparative example 7 Without lactic acid bacteria | | | |
|---|---|---|---|---|---|---|---|---|
| Day | 0 | 3 | 7 | 14 | 0 | 3 | 7 | 14 |
| Subject A | ● | ● | ● | ● | ● | ● | ● | ● |
| Subject B | ● | ● | ● | ● | ● | ● | ● | ● |
| Subject C | ● | ● | ● | ● | ● | ● | ● | ● |

FIG. 8

TOPICAL COMPOSITION AND METHOD OF IMPROVING SKIN DISEASES AND DERMATITIS USING THE SAME

CROSS-REFERENCE TO RELATED APPLICATION

This application claims priority to Taiwan Application Serial Number 109122130, filed Jun. 30, 2020, which is herein incorporated by reference in its entirety.

BACKGROUND

Field of Invention

The present invention relates to a topical composition. More specifically, the present invention relates to a topical composition for skin and a method of improving skin diseases such as atopic dermatitis and acne using the same.

Description of Related Art

As the largest organ of a human body, skin can not only prevent water loss, adjust body temperature and generate cutaneous sensation, but also serve as a barrier. In addition to the physiological factors (e.g., hormones, nutrients and oil secretion) and environmental conditions (e.g., humidity, sunlight and weather), microorganisms on the skin also play an important role in affecting skin health. If the microorganisms on the skin can strike an ecological balance, the skin can stay healthy. However, if pathogens on the skin achieve a growth advantage, skin diseases are easily caused. For example, *Staphylococcus aureus* is associated with the occurrence of atopic dermatitis and eczema, and *Propionibacterium acnes* is associated with the occurrence of acne vulgaris. Common symptoms of skin diseases include itching, inflammation, dryness and the like, and scratching or touching of the affected skin easily causes a wound, or even triggers a more serious inflammation.

At present, common strategies for treating skin diseases can be classified as follows: (i) administration of steroids at different strengths (potencies) to inhibit the topical inflammation, (ii) administration of antibiotics to inhibit the growth of pathogens on the skin, and (iii) administration of antihistamine drugs to stop itching. However, long-term use of the drug such as steroids, antibiotics and/or an antihistamine may lead to the side effects such as skin atrophy, skin thinning, telangiectasia, dermatomyositis and/or pigmentation.

Therefore, it is imperative to find an alternative way to replace the conventional pharmaceutical treatment. Probiotics are one of the research targets for the treatment of skin diseases, and among them, lactic acid bacteria have considerable potential. Lactic acid bacteria can change the concentration of hydrogen ions in the microenvironment by metabolizing carbohydrates into organic acids such as lactic acid and/or acetic acid, to inhibit the growth of other bacteria. However, to improve skin diseases through the bacteriostasis of lactic acid bacteria, it is essential to retain the viability of lactic acid bacteria, thus imposing many limitations on the processes or dosage forms of products. Moreover, it is not easy to evaluate or preserve the activity of lactic acid bacteria in the products, so that problems may easily occur in quality control and/or long-term storage of the products.

In the view of above, it is necessary to provide a composition including a fermented product of lactic acid bacteria synbiotics so as to effectively improve the aforementioned shortcomings.

SUMMARY

Accordingly, one aspect of the present invention provides a topical composition having a fermented product of lactic acid bacteria synbiotics as an active ingredient, in which the fermented product of lactic acid bacteria synbiotics is obtained by performing a fermenting step with a lactic acid bacteria strain and a deactivating step. The aforementioned fermented product of lactic acid bacteria synbiotics is deactivated, but still can effectively inhibit the growth of *Staphylococcus aureus* and/or *Propionibacterium acnes*.

In another aspect, the present invention provides a method of improving skin diseases by using a fermented product of lactic acid bacteria synbiotics, in which the fermented product of lactic acid bacteria synbiotics is obtained by performing a fermenting step with a specific lactic acid bacteria strain and a deactivating step. The aforementioned fermented product of lactic acid bacteria synbiotics can effectively inhibit the growth of *Staphylococcus aureus* and/or *Propionibacterium acnes*.

In the other aspect, the present invention provides a method of improving dermatitis by using a fermented product of lactic acid bacteria synbiotics in which the fermented product of lactic acid bacteria synbiotics is obtained by performing a fermenting step with a lactic acid bacteria strain and a deactivating step. The aforementioned fermented product of lactic acid bacteria synbiotics increases the secretion amount of TGF-β and IL-10.

According to the aforementioned aspect, the present invention provides a topical composition, in which an active ingredient of the topical composition can be sourced from a fermented product of lactic acid bacteria synbiotics. The aforementioned fermented product of lactic acid bacteria synbiotics is obtained by performing a fermenting step with lactic acid bacteria and a deactivating step on a fermenting substrate. The aforementioned lactic acid bacteria are deposited in the Bioresource Collection and Research Center (BCRC) of Food Industry Research and Development Institute and China Center for Type Culture Collection (CCTCC) or China General Microbiological Culture Collection Center (CGMCC), and are consisting of *Lactobacillus salivarius* subsp. *salicinius* AP-32 (accession number BCRC910437 or CCTCC M 2011127), *Bifidobacterium animalis* subsp. *lactis* CP-9 (accession number BCRC910645 or CCTCC M 2014588) and *Lactobacillus acidophilus* TYCA06 (accession number BCRC91081 or CGMCC 152103). The aforementioned fermenting substrate may include protein and/or plant extracts.

According to another aspect, the present invention provides a method for improving skin diseases by using a fermented product of lactic acid bacteria synbiotics, in which the fermented product of lactic acid bacteria synbiotics is obtained by performing a fermenting step with lactic acid bacteria and a sterilizing step on a fermenting substrate. The aforementioned lactic acid bacteria are consisting of *Lactobacillus salivarius* subsp. *salicinius* AP-32 (accession number BCRC910437 or CCTCC M 2011127), *Bifidobacterium animalis* subsp. *lactis* CP-9 (accession number BCRC910645 or CCTCC M 2014588) and *Lactobacillus acidophilus* TYCA06 (accession number BCRC910813 or CGMCC 15210). The aforementioned fermenting substrate may include protein and/or plant extracts.

According to another aspect, the present invention provides a method of improving dermatitis by using a fermented product of lactic acid bacteria synbiotics, in which the fermented product of lactic acid bacteria synbiotics is obtained by performing a fermenting step with lactic acid bacteria and a deactivating step on a fermenting substrate. The aforementioned lactic acid bacteria are consisting of *Lactobacillus salivarius* subsp. *salicinius* AP-32 (accession number BCRC910437 or CCTCC M 2011127), *Bifidobacterium animalis* subsp. *lactis* CP-9 (accession number BCRC910645 or CCTCC M 2014588) and *Lactobacillus acidophilus* TYCA06 (accession number BCRC910813 or CGMCC 15210). The aforementioned fermenting substrate may include protein and/or plant extracts. The aforementioned fermented product of lactic acid bacteria synbiotics increases the secretion of IL-10 and TGF-$\beta$.

In one embodiment of the present invention, the protein includes animal protein and/or plant protein, in which the animal protein includes milk, milk powder and casein, and the plant protein includes soybeans and soybean products.

In one embodiment of the present invention, the plant extracts are selected from a group consisting of chamomile, wormwood, green tea, calendula, centella, and any combination thereof.

In one embodiment of the present invention, the fermented product of lactic acid bacteria synbiotics may include a fermentation broth, in which the effective dose of the fermentation broth may be, for example, 2 weight % (wt %) to 30 wt %.

In one embodiment of the present invention, the fermented product of lactic acid bacteria synbiotics may include a dried fermented product, in which the effective dose of the dried fermented product may be, for example, 0.4 wt % to 6.0 wt %.

In one embodiment of the present invention, the aforementioned topical composition may be, for example, a pharmaceutical composition or a cosmetic composition.

In one embodiment of the present invention, the dosage form of the aforementioned topical composition may be, for example, a tablet, a capsule, a powder, a cream, a spray, a gel, a solution, a granule, a cream or a lotion.

In one embodiment of the present invention, the protein includes animal protein and/or plant protein, in which the animal protein includes milk, milk powder and casein, and the plant protein includes soybeans and soybean products.

In one embodiment of the present invention, the plant extracts are selected from a group consisting of chamomile, wormwood, green tea, calendula, centella, and any combination thereof.

In one embodiment of the present invention, the fermented product of lactic acid bacteria synbiotics inhibits the growth of *Staphylococcus aureus* and *Propionibacterium acnes*.

Applying the topical composition of the present invention can not only solve the problem of quality control but also effectively inhibit *Staphylococcus aureus* and *Propionibacterium acnes* as well as increase the secretion of anti-inflammatory factors. Therefore, the topical composition has the potential of improving skin diseases such as atopic dermatitis and acne.

BRIEF DESCRIPTION OF THE DRAWINGS

The invention can be more fully understood by reading the followed detailed description of the embodiment, with reference made to the accompanying drawings as follows:

FIG. 8 was topical appearance photos illustrating the affected skin with acne vulgaris at different days after administering the gel in accordance with one embodiment of the present invention.

DETAILED DESCRIPTION

Figure 1A:
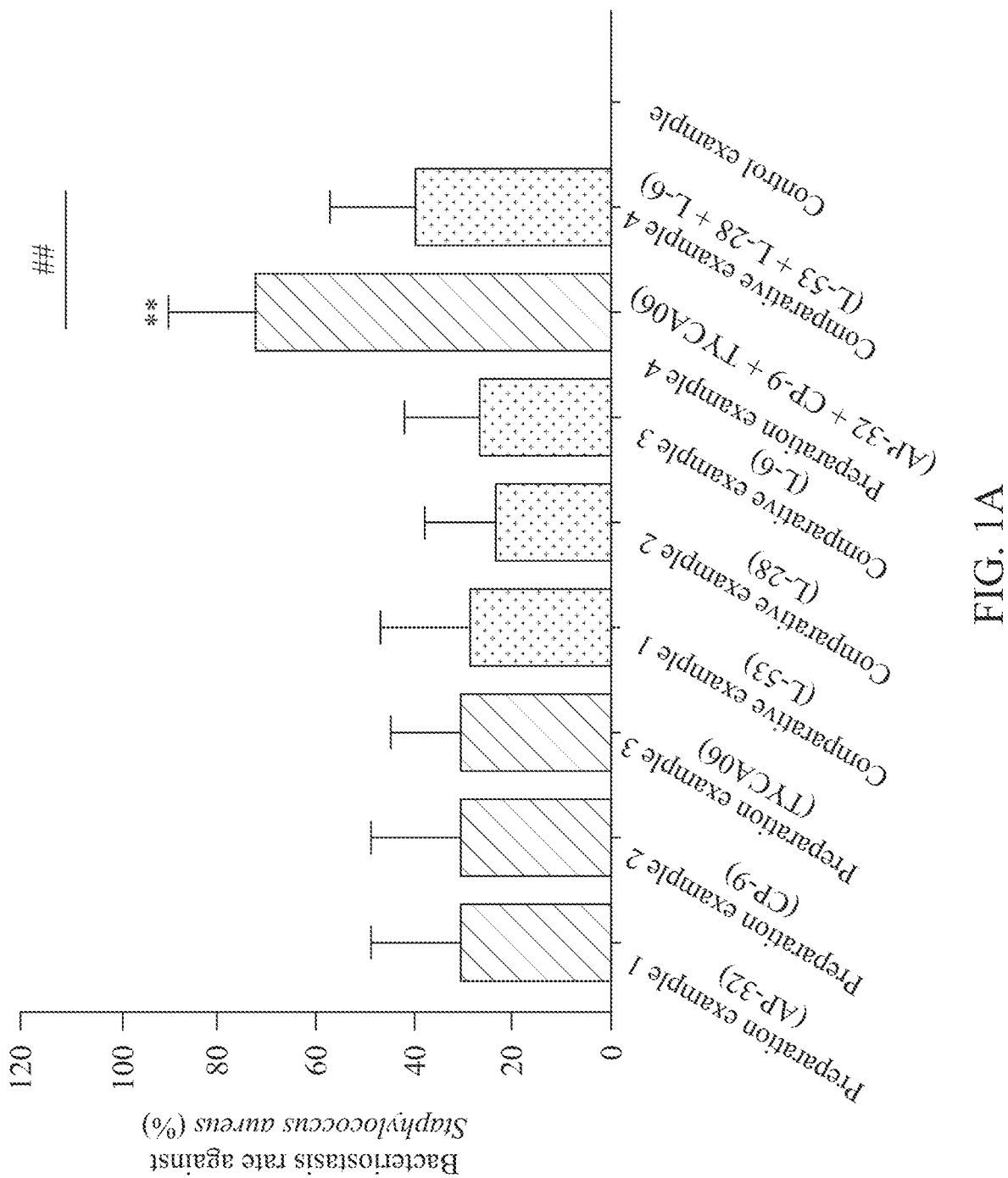
FIGS. 1A to 1C were bar charts illustrating the bacteriostasis rates against *Staphylococcus aureus* (FIG. 1A), *Propionibacterium acnes* (FIG. 1B) and *Candida albicans* (FIG. 1C) in accordance with one embodiment of the present invention.

As mentioned above, the present invention provides a topical composition, in which the topical composition may include an active ingredient sourced from a fermented product of lactic acid bacteria synbiotics. The fermented product of lactic acid bacteria synbiotics is obtained by performing a fermenting step with lactic acid bacteria and a deactivating step on a fermenting substrate. The aforementioned fermented product of lactic acid bacteria synbiotics can inhibit the growth of skin pathogens and increase the secretion of anti-inflammatory factors. In addition, since the lactic acid bacteria of the fermented product of lactic acid bacteria synbiotics are deactivated, the topical composition of the present invention is biologically safe and makes dose control and storage easier.

The "synbiotics" refer to a mixture of probiotics and prebiotics, in which the prebiotics can be metabolized by the probiotics so that the probiotics can grow and activate. In the present invention, the probiotics may be, for example, lactic acid bacteria, and the prebiotics may be, for example, a fermenting substrate. After culturing the lactic acid bacteria in the fermenting substrate in an environment simulating the intestine in vitro, the fermenting substrate can be metabolized by the lactic acid bacteria so as to obtain a fermented product of lactic acid bacteria synbiotics.

The aforementioned "lactic acid bacteria" may be consisting of *Lactobacillus salivarius* subsp. *salicinius*, *Bifidobacterium animalis* subsp. *lactis* and *Lactobacillus acidophilus*. In an example, the aforementioned lactic acid bacteria are deposited in the Bioresource Collection and Research Center (BCRC) of Food Industry Research and Development Institute (Address: No. 331, Shipin Road, Hsinchu, Taiwan) and are consisting of *Lactobacillus salivarius* subsp. *salicinius* AP-32 (Deposit Date: Jul. 30, 2009;

Accession number: BCRC910437), *Bifidobacterium animalis* subsp. *lactis* CP-9 (Deposit Date: Aug. 21, 2014; Accession number: BCRC910645), and *Lactobacillus acidophilus* TYCA06 (Deposit Date: Jan. 18, 2018; Accession number: BCRC910813) (hereinafter referred to as AP-32 strain, CP-9 strain and TYCA06 strain, respectively). The aforementioned lactic acid bacteria are also deposited in the China Center for Type Culture Collection (CCTCC) (Address: China Center for Type Culture Collection in Wuhan, China; Postal Code: 430072) or China General Microbiological Culture Collection Center (CGMCC) (Address: Institute of Microbiology, Chinese Academy of Sciences, Beijing, China; Postal Code: 100101), in which the *Lactobacillus salivarius* subsp. *salicinius* AP-32, *Bifidobacterium animalis* subsp. *lactis* CP-9 and *Lactobacillus acidophilus* TYCA06 are respectively deposited on Apr. 10, 2011, Nov. 24, 2014 and Jan. 15, 2018 under accession numbers CCTCC M 2011127, CCTCC M 2014588 and CGMCC 15210, respectively.

The aforementioned "fermenting substrate" may be, for example, a liquid fermenting substrate, a solid fermenting substrate or a semi-solid fermenting substrate including protein and/or plant extracts. In an example, the protein can be sourced from animal protein, which may be, for example, milk, powder and casein. In an example, the protein can be sourced from plant proteins, which may be, for example, soybeans and soybean products. In an example, the plant extracts can be extracted by a conventional method from a plant selected from the group consisting of chamomile, wormwood, green tea, calendula, centella, and any combination thereof. The aforementioned extraction method may be, for example, performed by using any pharmaceutically or cosmetically available extraction solvent (e.g., water or alcohol).

The aforementioned "fermenting step" may be, for example, performed in the conventional fermenting conditions to obtain a fermented bacteria solution of lactic acid bacteria synbiotics. Since the CP-9 strain is an anaerobe while the AP-32 strain and TYCA06 strain are facultative anaerobes, and the AP32 strain, CP-9 strain and TYCA06 strain prefer to grow at 37° C. Thus, the fermenting step is performed in an anaerobic environment at 37° C.

Then, the fermented bacteria solution of lactic acid bacteria synbiotics is subjected to a deactivating step to obtain a fermented product of lactic acid bacteria synbiotics. The deactivating step may include sterilization treatment and/or separation treatment, in which the sterilization treatment may be performed by a conventional sterilization method such as hot sterilization, and the separation treatment may be performed by a conventional separation method such as centrifugation. In an example, the sterilization treatment is performed at 100° C. The aforementioned fermented product of lactic acid bacteria synbiotics includes a fermentation broth and a dried fermented product, in which the fermentation broth includes, but is not limited to, a deactivated fermentation broth obtained after performing sterilization treatment on the fermented bacteria solution of lactic acid bacteria synbiotics, or a cell-removed fermentation broth obtained after performing centrifugation treatment and sterilization treatment on the fermented bacteria solution of lactic acid bacteria synbiotics, and the dried fermented product is obtained by further performing a drying step and/or a grinding step with a conventional method on the fermentation broth. The aforementioned drying step may be performed by a conventional drying method, e.g., freeze drying, vacuum drying or spray drying. The aforementioned grinding step may be performed by a conventional grinding method, e.g., mechanical grinding, roller grinding and/or flowing gas grinding.

When the fermentation broth is applied to the topical composition, the effective dose may be, for example, 2 wt % to 30 wt %. If the amount of the fermentation broth in the topical composition is too low (e.g., lower than 2 wt %), the topical composition cannot effectively inhibit skin pathogens and/or increase the water content of the skin. If the amount of the fermentation broth in the topical composition is too high (e.g., higher than 30 wt %), the topical composition causes an allergic reaction of the skin.

When the aforementioned dried fermented product is applied to the topical composition, the effective dose of the dried fermented product may be, for example, greater than 0.4 wt %. In some specific examples, the effective dose of the dried fermented product may be, for example, 0.4 wt % to 6 wt %. If the amount of the dried fermented product in the topical composition is too low (e.g., lower than 0.4 wt %), the topical composition cannot effectively inhibit the effects of skin pathogens and/or increase the water content of the skin. If the amount of the dried fermented product in the topical composition is too high (e.g., higher than 6 wt %), the topical composition causes an allergic reaction of the skin.

It should be noted that the AP-32 strain, CP-9 strain and TYCA06 strain can be co-cultured to obtain a fermented product of mixed lactic acid bacteria synbiotics. In addition, the fermented product of mixed lactic acid bacteria synbiotics can be obtained by mixing the fermentation broths or the dried fermented products of the AP-32 strain, CP-9 strain and TYCA06 strain.

The "skin pathogens" refer to the microorganisms that may cause diseases of the skin, e.g., *Staphylococcus aureus*, *Propionibacterium acnes* and *Candida albicans*. The "anti-inflammatory factors" refer to immunosuppressive cytokines, which may be, for example, interleukin-10 (IL-10) and transforming growth factor beta (TGF-β).

In one embodiment, the aforementioned topical composition is a pharmaceutical composition or a cosmetic composition. In an example, the topical composition may optionally include but not limited to pharmaceutically or cosmetically available carriers, excipients, diluents, adjuvants, and/or additives.

In one embodiment, the aforementioned topical composition may optionally include a gelling agent, e.g., natural Sephadex, Carbomer, a xanthan gum and/or ammonium acryloyldimethyltaurate. In an example, the topical composition may optionally include plant extracts, e.g., aloe, soybeans, *Houttuynia cordata, Scutellaria baicalensis* root, neem (*Azadirachta indica*) leaves, *Rehmannia chinensis* root, white willow bark, *Phellodendron amurense* bark, *Usnea barbata*, thyme, liquorice (*Glycyrrhiza uralensis*), pumpkin seeds, mint, torbangun (*Plectranthus amboinicus*), lemon and/or a fermentation broth of pear juice.

In one embodiment, the aforementioned topical composition may optionally include a preservative, e.g., dipropylene glycol, hydroxyacetophenone, caprylyl glycol, dipotassium glycyrrhizinate, mono-caprylin glycerate, ethylhexylglycerin, hydrogenated castor oil, butylene glycol, propylene glycol, glycolic acid, caprylyl glycol, p-hydroxyacetophenone, PEG-40 and/or PEG-60.

In one embodiment, the aforementioned topical composition may optionally include plant oil, e.g., palmitic acid, isononyl isononanoate, shea butter, almond oil, menthol oil and/or tea tree essential oil.

In one embodiment, the aforementioned topical composition may optionally include a humectant, e.g., sodium hyaluronate and/or allantoin. In one embodiment, the aforementioned topical composition may optionally include a diluent, e.g., sodium hydroxide, spring sea water and/or glycerin.

In one embodiment, the dosage form of the aforementioned topical composition is not limited and may be, for example, a tablet, a capsule, a powder, a cream, a spray, a gel, a solution, a pulvis, or a lotion.

Experiments have proved that the effectiveness of the mixed fermented products of lactic acid bacteria synbiotics of AP-32 strain, CP-9 strain and TYCA06 strain exceeds the total effectiveness of the individual fermented products of lactic acid bacteria synbiotics of AP-32 strain, CP-9 strain and TYCA06 strain regarding to inhibiting the growth of skin pathogens, such as *Staphylococcus aureus* and *Propionibacterium acnes*. Furthermore, cell experiments have proved that the aforementioned fermented product of lactic acid bacteria synbiotics can effectively increase the secretion amount of anti-inflammatory factors such as IL-10 and TGF-β. In addition, after the topical composition including the aforementioned fermented product of lactic acid bacteria synbiotics is applied to the affected skin, the inflammation and itching degree of atopic dermatitis and acne can be significantly reduced, and the rate of wound healing is effectively increased. Therefore, the fermented product of lactic acid bacteria synbiotics of the present invention can be applied to the topical composition to improve the uncomfortable symptoms of atopic dermatitis and acne vulgaris.

Several examples are used below to describe the application of the present invention, but are not intended to limit the present invention. Those skilled in the art to which the present invention belongs may make various variations and modifications without departing from the spirit and scope of the present invention.

Example 1. Bacteriological Characteristics of Lactic Acid Bacteria

The species and bacteriological characteristics of lactic acid bacteria were analyzed by 16S rRNA sequential analysis and microbiological assay kit API, and the results were shown in Table 1.

TABLE 1

| Strain name | Morphological characteristics |
| --- | --- |
| *Lactobacillus salivarius* subsp. *salicinius* AP-32 (accession number: BCRC910437 or CCTCC M 2011127). | It was gram-positive bacillus which did not generate spores, had no catalase, oxidase or motility, and was able to grow in both aerobic and anaerobic environments. The optimal growth temperature was 37 ± 1° C. It belonged to a facultative heterofermentative strain and did not produce gas in glucose metabolism. While cultured in a Man Rogosa and Sharp (MRS) medium, the colony thereof had a white solid round shape, while the cell thereof had a short rod-like shape, and the two ends of the cell were round-shaped. It often appeared in a single cell. |
| *Bifidobacterium animalis* subsp. *lactis* CP-9 (accession number: BCRC910645 or CCTCC M 2014588) | It was gram-positive bacillus, which did not generate spores, had no catalase, oxidase or motility, and grew in an absolutely anaerobic environment. The optimal growth temperature was 37 ± 1° C. It belonged to a facultative heterofermentative strain, and did not produce gas in glucose metabolism. While cultured in an MRS medium, the colony thereof had a white solid round shape, while the cell thereof had a medium-long rod-like shape, and two ends of the cell were occasionally dichotomous branched (Y shaped or V-shaped). |
| *Lactobacillus acidophilus* TYCA06 (accession number: BCRC910813 or CGMCC 15210). | It was gram-positive bacillus, which did not generate spores, had no catalase, oxidase or motility, and was able to grow in both aerobic and anaerobic environments. The optimal growth temperature was 37 ± 1° C. It belonged to a facultative heterofermentative strain, and did not produce gas during glucose metabolism. While cultured in an MRS medium, the colony thereof had a translucent irregular shape, while the cell thereof had a medium-rod shape, and two ends of the cell were round-shaped. It often appeared in a single chain or short-chains. |

Example 2. Preparation of Fermentation Broth and Fermentation Powder

Firstly, strains Nos. 1 to 6 of lactic acid bacteria, namely, *Lactobacillus salivarius* subsp. *salicinius* AP-32, *Bifidobacterium animalis* subsp. *lactis* CP-9, *Lactobacillus acidophilus* TYCA06, *Lactobacillus salivarius* subsp. *salicinius* L-53, *Bifidobacterium animalis* subsp. *lactis* L-28 and *Lactobacillus acidophilus* L-6 respectively were obtained, in which the strains L-53, L-28 and L-6 were provided by glac Biotech Co., Ltd, Taiwan. The aforementioned strains Nos. 1 to 6 were spread on an MRS medium agar individually to obtain single colonies.

The single colonies of strains Nos. 1 to 6 were inoculated in a fermenting substrate respectively, and a fermenting step was performed at 37° C. to obtain a lactic acid bacteria solution (LAB solution), in which the LAB solution contained about $10^9$ CFU/mL to $10^{10}$ CFU/mL bacteria. The aforementioned fermenting substrate was an MRS culture solution including protein and/or plant extracts, in which the protein may be derived from animal protein and plant protein. The animal protein may be derived from milk, milk powder and casein, and the plant protein may be derived from soybeans, soybean products and the like. The aforementioned plant extracts could be extracted by a conventional method from a plant selected from a group consisting of chamomile, wormwood, green tea, calendula, centella, and any combination thereof. Since the usage amounts of the protein and plant extracts are well known to one of the ordinary skills in the art to the present invention and could be adjusted depending on practical requirements without affecting the progress of the fermenting step, the usage amounts of the protein and plant extracts would not be elaborated herein. In this example, strains Nos. 1 to 6 were subjected to the fermenting step with the same fermenting substrate. The LAB solution was centrifuged for 10 minutes at a temperature of 4° C. with a rotation speed of 3,000 rpm (rotation per minute) so as to obtain a cell-removed fermentation broth. Then, the cell-removed fermentation broth was subjected to a sterilizing step for 30 minutes at 100° C. to obtain a fermentation broth. After that, the fermentation broth was subjected to a drying step and a grinding step to obtain a fermentation powder, in which the fermentation powder may be regarded as a five-fold concentrate of the fermentation broth.

Example 3. Bacteriostasis Rate of Single-Strain or Multi-Strain Fermentation Powder Against Skin Pathogens The fermentation powders of strains Nos. 1 to 6 were made into 4 wt % fermentation powder solutions with pure water respectively so as to obtain preparation example 1, preparation example 2, preparation example 3, comparative example 1, comparative example 2 and comparative example 3. Preparation example 1, preparation example 2 and preparation example 3 of equal amount were mixed so as to obtain preparation example 4, in which preparation example 4 contained 4 wt % of the fermentation powder. Comparative example 1, comparative example 2 and comparative example 3 of equal amount were mixed so as to obtain comparative example 4, in which the comparative example 4 contained 4 wt % of the fermentation powder. Pure water was used as a control example.

Solutions of pathogens *Staphylococcus aureus, Propionibacterium acnes* and *Candida albicans*, were prepared respectively (concentration: $1\times10^5$ CFU/mL to $9\times10^5$ CFU/mL). Pathogen culture solutions were obtained by respectively adding 100 μl of each pathogen solution into 25 mL of preparation example 1, preparation example 2, preparation example 3, preparation example 4, comparative example 1, comparative example 2, comparative example 3, comparative example 4 or control example, followed by a fermenting step for 20 minutes at 37° C. The aforementioned pathogen culture solutions were properly diluted, spread on an MRS agar medium and cultured for 48 hours to 72 hours at 37° C. to obtain pathogen colonies.

The numbers of the pathogen colonies of *Staphylococcus aureus, Propionibacterium acnes* and *Candida albicans* were counted respectively, and the bacteriostasis rates (Z) were calculated by the formula (1).

$$Z=(1-X/Y)\times100\% \tag{1}$$

in this example, X of the formula (1) represented the number of pathogen colonies of the preparation example or comparative example, and Y of the formula (1) represented the number of pathogen colonies of the control example.

Figure 1B:
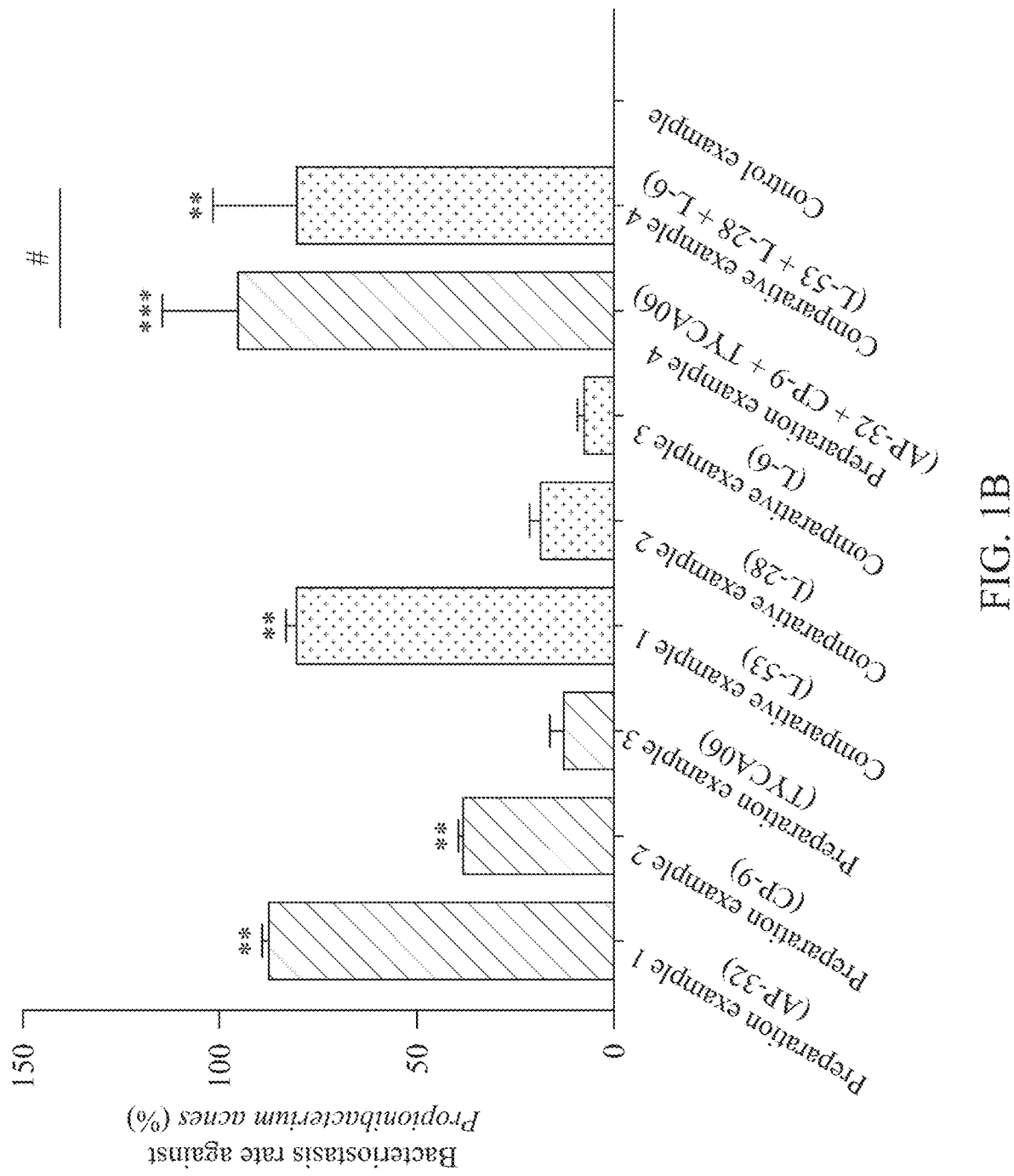
Figure 1C:
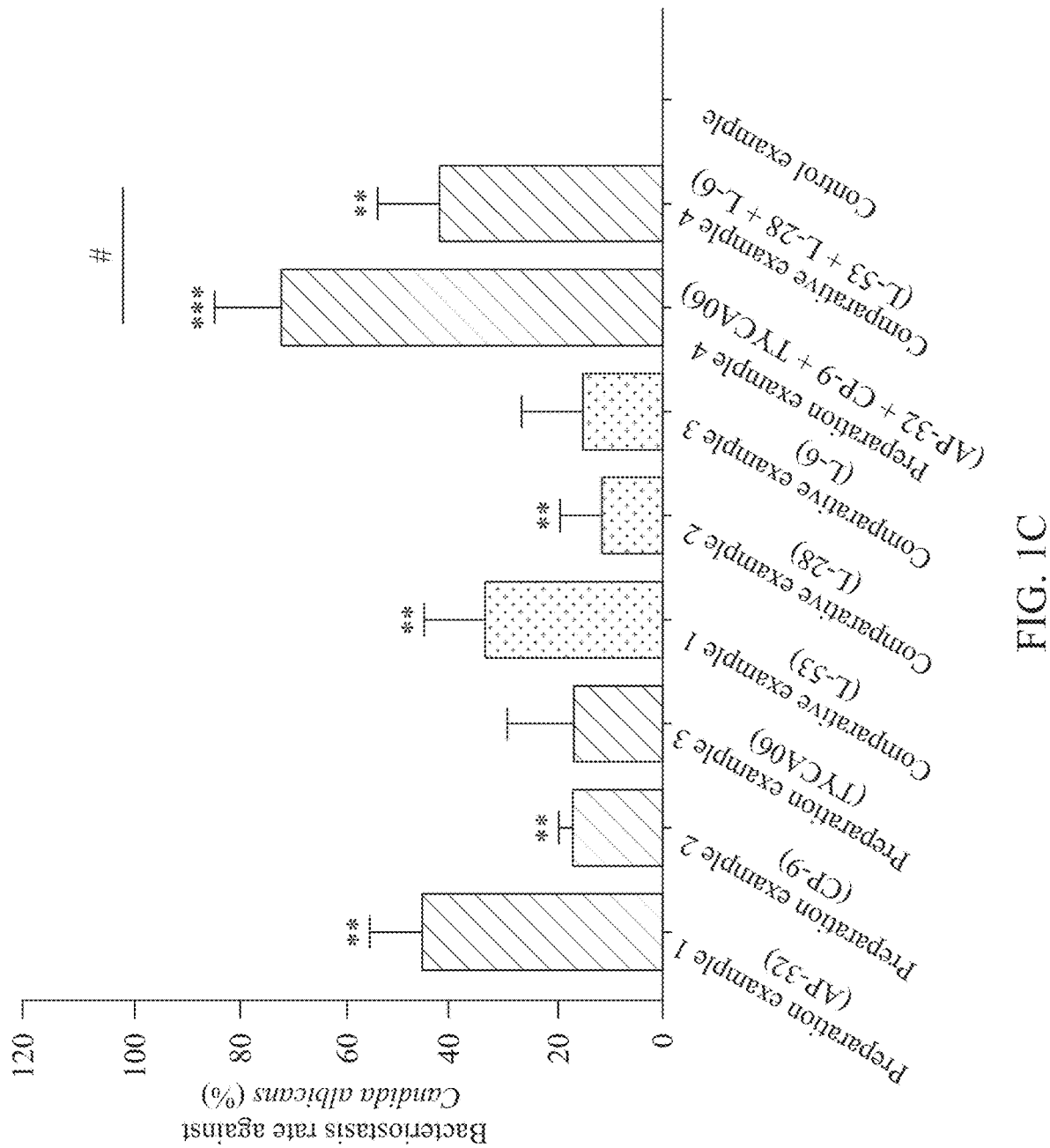

FIGS. 1A to 1C were bar charts illustrating the bacteriostasis rates against *Staphylococcus aureus* (FIG. 1A), *Propionibacterium acnes* (FIG. 1B) and *Candida albicans* (FIG. 1C) in accordance with one embodiment of the present invention, in which the horizontal axis represented group, the vertical axis represented bacteriostasis rate, "*", "" and "*" indicated statistically significant differences between the control example and the preparation example or comparative example according to student's t-test statistical analysis ($p<0.05$, $p<0.01$ and $p<0.001$, respectively), and "#" and "###" indicated a statistically significant difference between preparation example 4 and comparative example 4 according to student's t-test statistical analysis ($p<0.05$ and $p<0.01$, respectively). As shown in FIG. 1A, the bacteriostasis rates of preparation example 1, preparation example 2, preparation example 3, comparative example 1, comparative example 2 and comparative example 3 were 30.2%, 30.2%, 30.4%, 28.6%, 23.3% and 26.6%, respectively. The bacteriostasis rates of preparation example 4 and comparative example 4 were 72% and 40%, respectively. According to the statistic results, the bacteriostasis rate of preparation example 4 was significantly greater than that of the control example, showing that the fermentation powders of a mixture of different strains is more effective than that of mixtures of individual strains in inhibiting the growth of *Staphylococcus aureus*. In addition, despite the same species of the lactic acid bacteria used in preparation example 4 and comparative example 4, preparation example 4 and comparative example 4 had significant difference therebetween in the bacteriostasis rates, showing that the strains (Nos. 1 to 3) of the present invention were necessarily mixed in the fermentation powders to effectively inhibit the growth of *Staphylococcus aureus*.

As shown in FIG. 1B, the bacteriostasis rates of preparation example 1, preparation example 2, preparation example 3, comparative example 1, comparative example 2 and comparative example 3 were 87.6%, 37.7%, 12%, 80.4%, 18.1% and 7.0%, respectively, and the bacteriostasis rates of preparation example 4 and comparative example 4 were 95% and 80.2%, respectively. Compared with preparation example 1, preparation example 2, preparation example 3, comparative example 1, comparative example 2, comparative example 3 and comparative example 4, preparation example 4 had a higher bacteriostasis rate, showing that preparation example 4 could effectively inhibit the growth of *Propionibacterium acnes*.

As shown in FIG. 1C, the bacteriostasis rates of preparation example 1, preparation example 2, preparation example 3, comparative example 1, comparative example 2 and comparative example 3 were 45.2%, 16.1%, 16.1%, 33.7%, 11.3% and 15.2%, respectively, and the bacteriostasis rates of preparation example 4 and comparative example 4 were 71.1% and 42.2%, respectively. Compared with other groups, preparation example 4 had a higher bacteriostasis rate, showing that preparation example 4 could effectively inhibit the growth of *Candida albicans*.

As can be seen from the aforementioned experiment, the fermentation powders of the mixture of strains Nos. 1 to 3 had a better effect than the ones of single strains of Nos. 1 to 3 in inhibiting *Staphylococcus aureus, Propionibacterium acnes* and/or *Candida albicans*. In addition, the fermentation powders mixing different strains of the same species could not effectively inhibit the growth of the aforementioned skin pathogens, showing that only the mixed strains (Nos. 1 to 3) of the present invention could effectively inhibit the growth of the aforementioned skin pathogens.

Example 4. Evaluation of Anti-Inflammatory Effect of Fermentation Powder with in Vitro Cell Experiments Firstly, the fermentation powders of the aforementioned strains Nos. 1 3 were dissolved in water and then prepared as standard solutions in a cell culture medium with a concentration of 20 mg/mL of the fermentation powders. Next, 20 μl of each standard solution of strains Nos. 1 to 3 was mixed with $1\times10^6$ peripheral blood mononuclear cells (PBMCs) and 100 μl of the cell culture medium respectively to obtain preparation example 5, preparation example 6 and preparation example 7. Comparative example 5 was obtained by mixing 100 μl of the cell culture medium containing $1\times10^6$ PBMCs and 20 μl of pure water. Comparative example 5, preparation example 5, preparation example 6 and preparation example 7 were cultured for 48 hours at 37° C. and then centrifuged at 4° C. for 10 minutes at 3,000 rpm to obtain a supernatant. The amounts of TGF-β and IL-10 in the supernatant were measured by enzyme-linked immunosorbent assay (ELISA), and the results were shown in FIG. 2A and FIG. 2B.

Figure 2A:
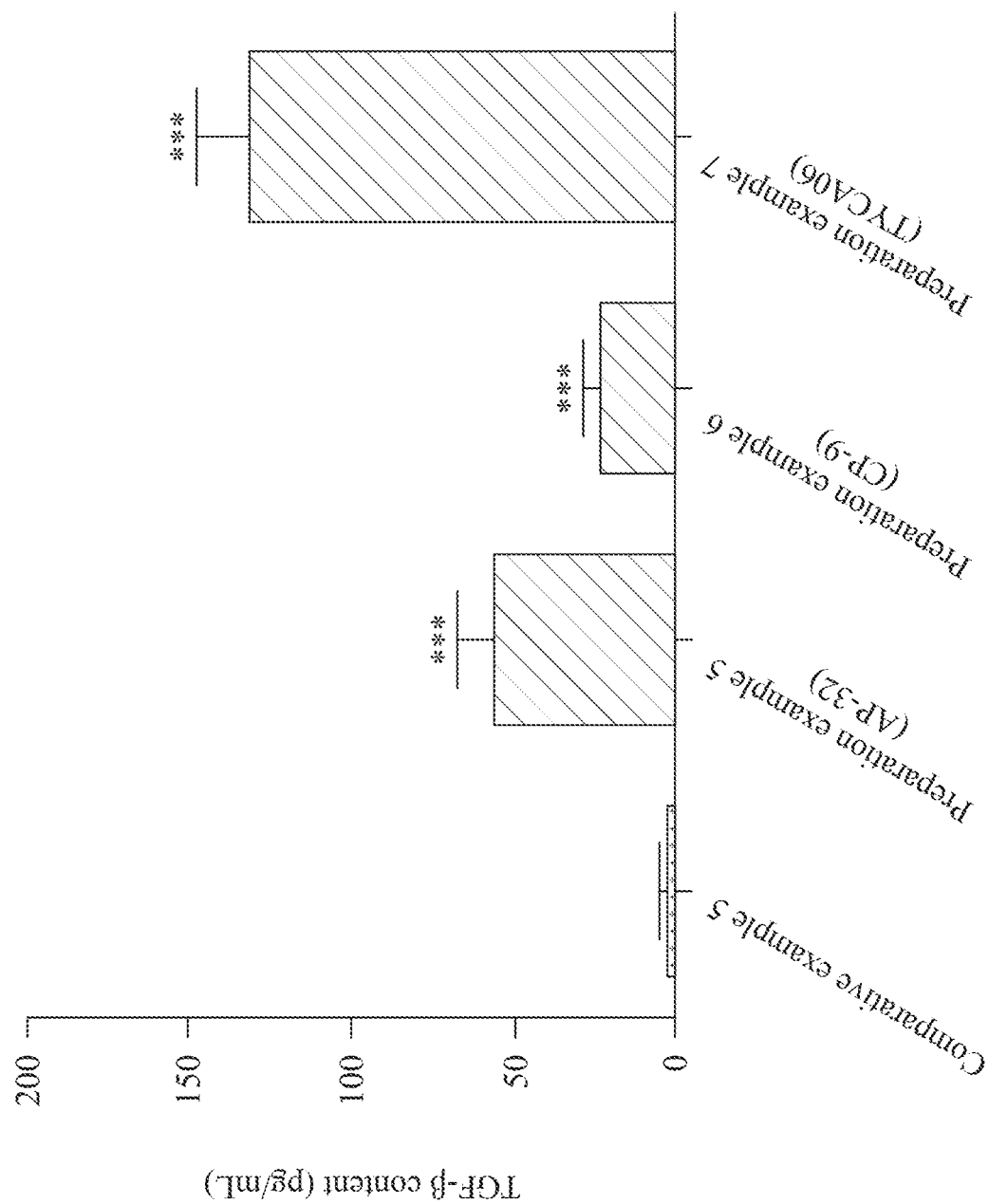
FIG. 2A and FIG. 2B were bar charts illustrating the amount of TGF-$\beta$ (FIG. 2A) and the amount of IL-10 (FIG. 2B) in accordance with one embodiment of the present invention.
Figure 2B:
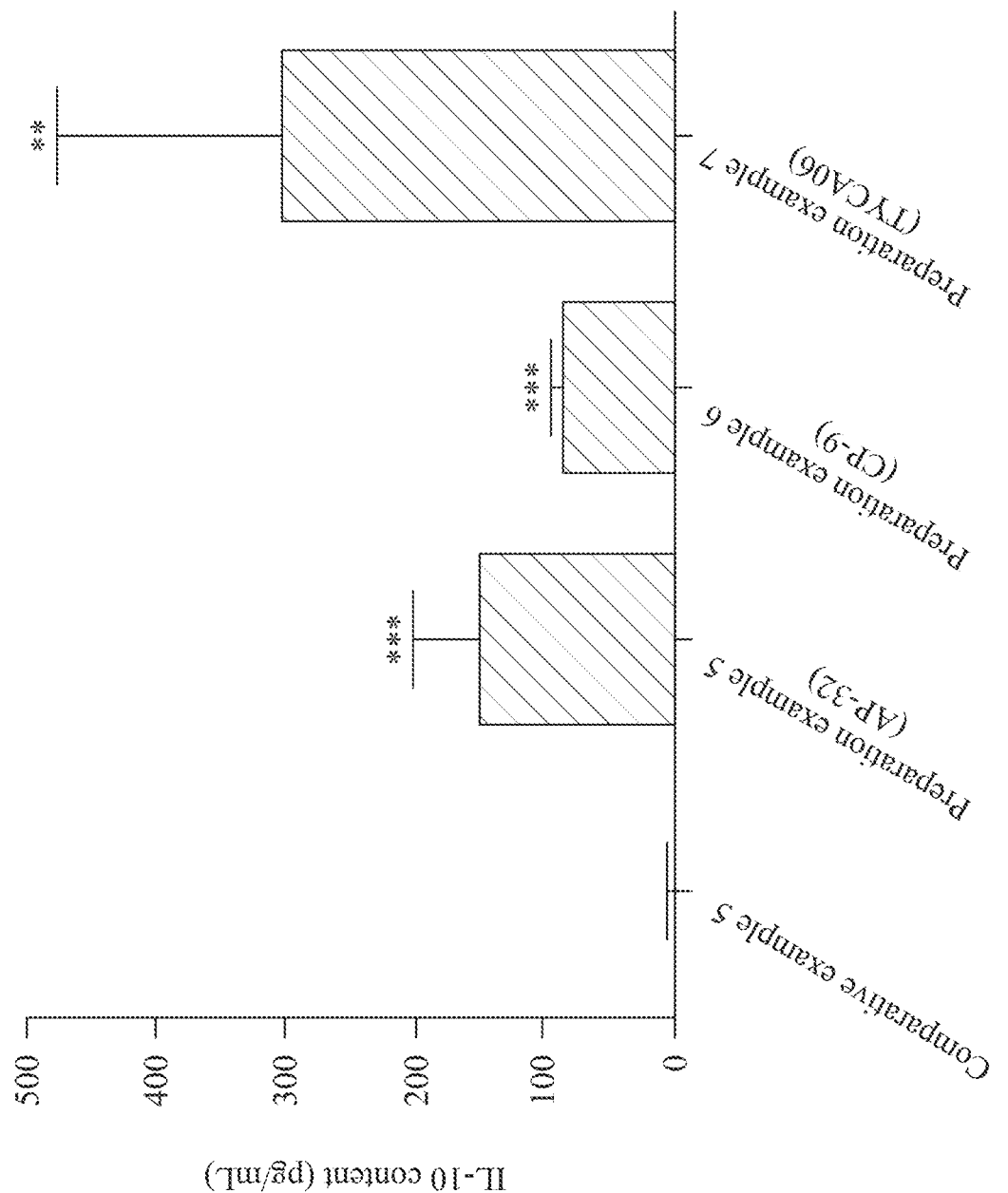

FIG. 2A and FIG. 2B were bar charts illustrating the amount of TGF-8 (FIG. 2A) and the amount of IL-10 (FIG. 2B) in accordance with one embodiment of the present invention, in which the horizontal axis represented groups, the longitudinal axis represented concentration (unit: pg/mL), and "" and "*" indicated statistically significant differences ($p<0.01$ and $p<0.001$, respectively) from comparative example 5 using student's t-test statistical analysis. As shown in FIG. 2A, the amounts of TGF-β in preparation example 5, preparation example 6 and preparation example 7 were 56.5 pg/mL, 23.2 pg/mL and 130.9 pg/mL, respectively, which were significantly greater than the amount of TGF-β in comparative example 5, showing that the fermentation powders of strains No. 1, No. 2 and No. 3 could effectively induce cells to secrete TGF-8.

As shown in FIG. 2B, the amounts of IL-10 in preparation example 5, preparation example 6 and preparation example 7 were 147.6 pg/mL, 84.2 pg/mL and 303.2 pg/mL, respectively, which were significantly greater than the amount of IL-10 in comparative example 5, showing that the fermentation powders of strains No. 1, No. 2 and No. 3 could effectively induce cells to secrete IL-10.

According to the aforementioned experiments, the fermentation powders of strains No. 1, No. 2 and No. 3 could effectively increase the secretion of immunosuppressive cytokines by cells, implying that the fermentation powders of strains No. 1, No. 2 and No. 3 were anti-inflammatory.

Example 5. Evaluation of Inhibitory Effect of Fermentation Powder-Containing Emulsion on the Growth of *Staphylococcus aureus*

The fermentation powders of strains No. 1, No. 2 and No. 3 were mixed in equal weights so as to obtain a mixed fermentation powder, which was subsequently used to prepare an emulsion. Based on the total weight of the emulsion, the emulsion included 2 wt % to 10 wt % of plant oil (including palmitic acid, isononyl isononanoate, shea butter and almond oil), 0.5 wt % to 1.5 wt % of natural plant extracts (aloe extract and zucchini seed extract), 2 wt % to 10 wt % of humectant (including sodium hyaluronate and allantoin), 0.5 wt % to 1.5 wt % of polyol preservative (including dipropylene glycol, hydroxyacetophenone, caprylyl glycol and dipotassium glycyrrhizinate), a 0.5 wt % to 1.5 wt % of gelling agent (including natural Sephadex, xanthan gum and Carbomer), 0.05 wt % to 10 wt % of diluent (including sodium hydroxide, spring sea water and glycerin) and balance water. Since all of the aforementioned additives were conventional ingredients and could be optionally adjusted depending on real requirements without affecting the bacteriostatic effect, the actual ingredient would not be elaborated herein.

To obtain preparation example 8 and comparative example 6, 100 μl of the *Staphylococcus aureus* solution (concentration of *Staphylococcus aureus*: $1\times10^5$ CFU/mL to $9\times10^5$ CFU/mL) was added into 2.5 mL of the above-mentioned emulsion and 2.5 mL of sterile water, respectively. After culturing for 20 minutes at 37° C., preparation example 8 and comparative example 6 were properly diluted and spread on a medium, followed by further 48 hours of culture incubation at 37° C. to obtain colonies of *Staphylococcus aureus*. The numbers of colonies of *Staphylococcus aureus* in preparation example 8 and comparative example 6 were counted respectively, and the bacteriostasis rates were calculated according to formula (I), in which X of the formula (1) represented the number of the colonies of *Staphylococcus aureus* in the preparation example, and Y of the formula (1) represented the number of the colonies of *Staphylococcus aureus* in the comparative example. The results were shown in FIG. 3.

Figure 3:
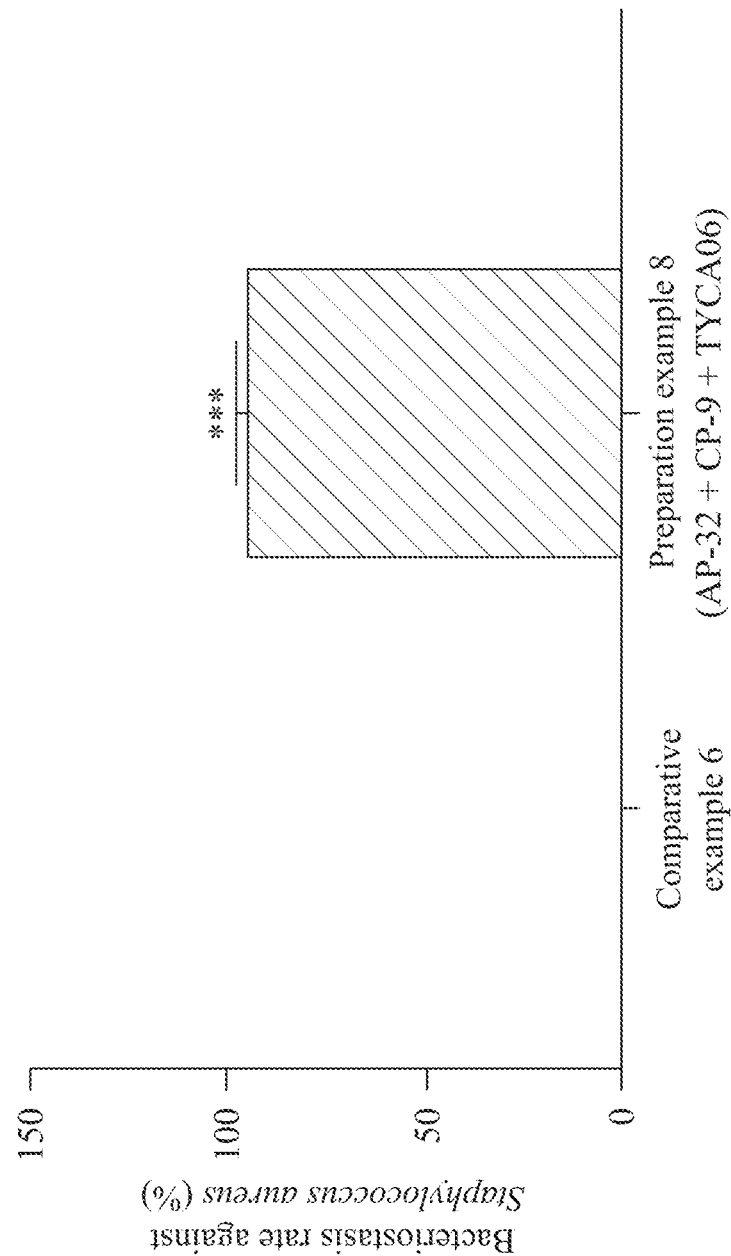
FIG. 3 was a bar chart illustrating the bacteriostasis rate against *Staphylococcus aureus* in accordance with one embodiment of the present invention.

FIG. 3 was a bar chart illustrating the bacteriostasis rate against *Staphylococcus aureus* in accordance with one embodiment of the present invention, in which the horizontal axis represented groups, the longitudinal axis represented bacteriostasis rates, and "***" indicated a statistically significant difference from comparative example 6 using student's t-test statistical analysis ($p<0.001$). As shown in FIG. 3, the bacteriostasis rate of preparation example 8 was 96%, which was significantly greater than that of comparative example 6, showing that the emulsion of preparation example 8 was able to effectively inhibit *Staphylococcus aureus*. Since *Staphylococcus aureus* was well-known to play an important role in the occurrence of atopic dermatitis, having the ability to inhibit *Staphylococcus aureus* indicated having the ability to improve uncomfortable symptoms of atopic dermatitis.

Example 6. Evaluation of Moisturizing Effect of Fermentation Powder-Containing Emulsion on Atopic Dermatitis Preparation example 9 and preparation example 10 were the aforementioned emulsions containing 0.2 wt % and 0.4 wt % of the mixed fermentation powder, respectively. The emulsions of comparative example 6, preparation example 9 and preparation example 10 were respectively applied to the cheek skin of a subject with atopic dermatitis. After the emulsions were applied, the subjects stayed under room temperature for 3 hours, and the moisture retained in the cheek skin of the subject was tested by an intelligent skin analysis system (Beijing Yi Li Mei Technology Co., Ltd, model ES3100), and the results were shown in FIG. 4.

Figure 4:
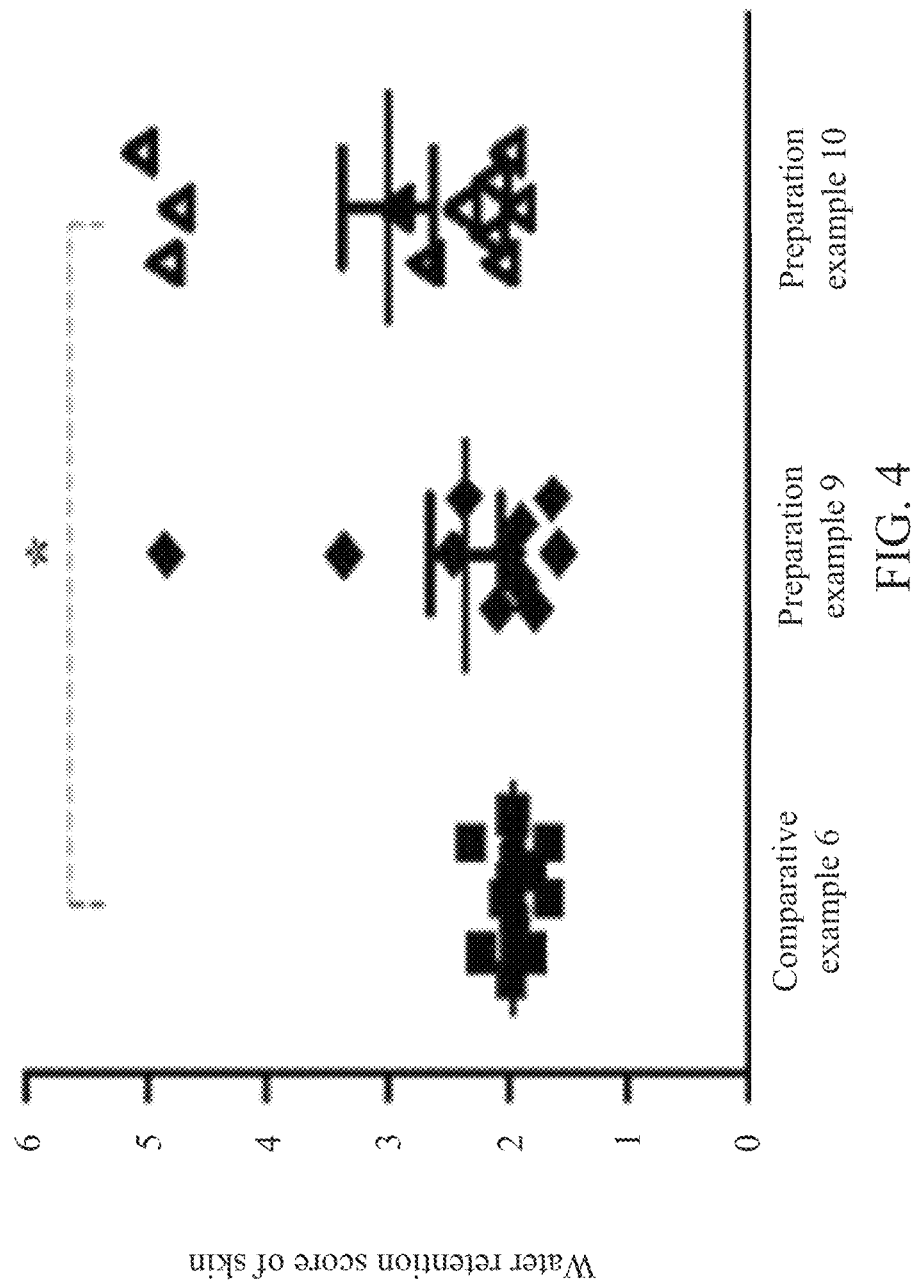
FIG. 4 was a scatter diagram illustrating the water retention score of skin in accordance with one embodiment of the present invention.

FIG. 4 was a scatter diagram illustrating the water retention score of skin in accordance with one embodiment of the present invention, in which the horizontal axis represented groups, the longitudinal axis represented water retention score of skin, and "*" indicated a statistically significant difference from comparative example 6 using student's t-test statistical analysis (p<0.05). As shown in FIG. 4, compared with comparative example 6, the water retention score of the skin of the subject of preparation example 10 was significantly increased, showing that the effective dose of the mixed fermentation powder was greater than or equal to 0.4 wt %.

Figure 5A:
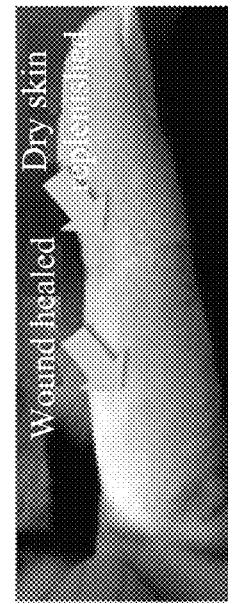
FIGS. 5A to 5D were topical appearance photos of the hand skin of a subject with atopic dermatitis before (FIG. 5A and FIG. 5B) and after (FIG. 5C and FIG. 5D) administering an emulsion in accordance with one embodiment of the present invention.
Figure 5B:
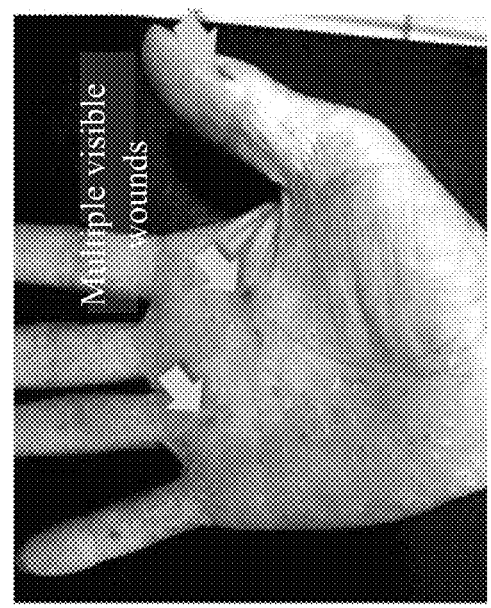
Figure 5C:
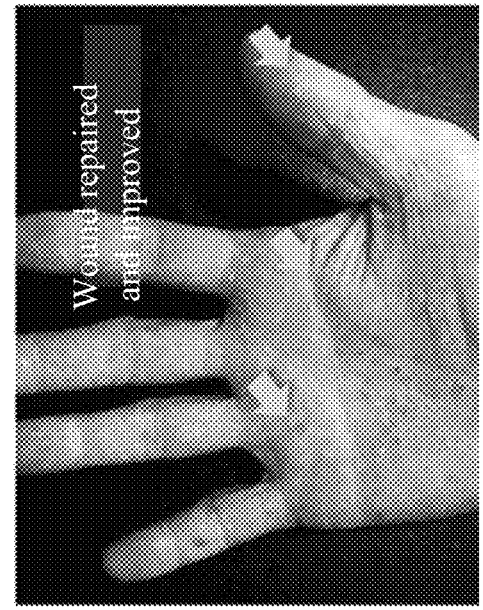
Figure 5D:
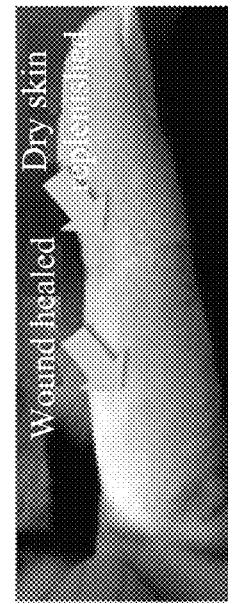

Example 7. Evaluation of Effect of Fermentation Powder-Containing Emulsion on Inhibiting Dermatitis FIGS. 5A to 5D were topical appearance photos of the hand skin of a subject with atopic dermatitis before (FIG. 5A and FIG. 5B) and after (FIG. 5C and FIG. 5D) administering an emulsion in accordance with one embodiment of the present invention, in which FIG. 5A and FIG. 5C respectively showed the topical skin of subject 1 before administration and after administration, and FIG. 5B and FIG. 5D respectively showed the topical skin of subject 2 before administration and after administration, the arrows indicated a wound or dry skin, and the emulsion used in this example was the aforementioned preparation example 10. Comparing FIG. 5A with FIG. 5C, drying skin and peeling skin at joints were obviously improved, and the wound healed well after the subject 1 was administered with the emulsion of preparation example 10. Comparing FIG. 5B with FIG. 5D, the wound of subject 2 pointed by the arrow healed well after administered with the emulsion of preparation example 10, showing that the emulsion of preparation example 10 could increase the healing rate of a wound on the skin with atopic dermatitis.

According to the aforementioned experiment, in addition to inhibit the growth of *Staphylococcus aureus*, the topical composition of the present invention could also increase the skin moisture as well as the wound healing rate of a subject with atopic dermatitis, showing that the topical composition of the present invention could improve the uncomfortable symptoms of atopic dermatitis.

Example 8. Evaluation of the Effect of Fermentation Broth-Containing Gel on Inhibiting Growth of *Propionibacterium acnes*

The fermentation broths of strains Nos. 1 to 3 in Example 2 were mixed in equal volume to form a mixed fermentation broth, which was then used to prepared a gel, in which the gel contained 5 wt % of the mixed fermentation broth. In addition, the aforementioned gel could contain various conventional additives. Based on the total weight of the gel, the gel included 1 wt % to 6 wt % of natural plant extracts [including extracts of soybeans, *Houttuynia cordata, Scutellaria baicalensis* root, neem (*Azadirachta indica*) leaves, *Rehmannia chinensis* root, white willow bark, *Phellodendron amurense* bark, fermentation broth of pear juice, *Usnea barbata*, thyme, liquorice (*Glycyrrhiza uralensis*), pumpkin seeds, aloe, mint and lemon extraction], 0.1 wt % to 0.5 wt % of humectant (including sodium hyaluronate and allantoin), 0.1 wt % to 1.5 wt % of polyol preservative (including mono-caprylin glycerate, ethylhexylglycerin, PEG-40, hydrogenated castor oil, glycolic acid, butylene glycol, propylene glycol, caprylyl glycol and p-hydroxyacetophenone), 0.3 wt % to 1 wt % of a gelling agent (including ammonium acryloyldimethyltaurate and Carbomer), 0.05 wt % to 1 wt % of diluent (including sodium hydroxide and spring sea water), and balance water. Since all of the aforementioned additives were conventional ingredients and could be optionally adjusted depending on practical requirements without affecting the bacteriostatic effect, the actual ingredient would not be elaborated herein.

To obtain preparation example 11 and comparative example 7, 100 µl of the *Propionibacterium acnes* solution was added into 2.5 g of the aforementioned gel and 2.5 mL of sterile water respectively, in which the aforementioned *Propionibacterium acnes* solution contained $1\times10^5$ CFU/mL to $9\times10^5$ CFU/mL *Propionibacterium acnes*. After culturing for 20 minutes in an anaerobic environment at 37° C., the aforementioned preparation example 11 and comparative example 7 were properly diluted with reverse osmosis water and spread on a tryptone soy agar (TSA) medium containing 5 wt % of sheep blood, followed by cultured for 48 to 72 hours of culture incubation in an anaerobic environment at 37° C. to obtain *Propionibacterium acnes* colonies. The numbers of the colonies of *Propionibacterium acnes* were counted respectively, and the bacteriostasis rates were calculated according to formula (I), in which in this example, X of the formula (1) represented the number of the colonies of *Propionibacterium acnes* in the preparation example, and Y of the formula (1) represented the number of the colonies of *Propionibacterium acnes* in the comparative example. The results were shown in FIG. 6.

Figure 6:
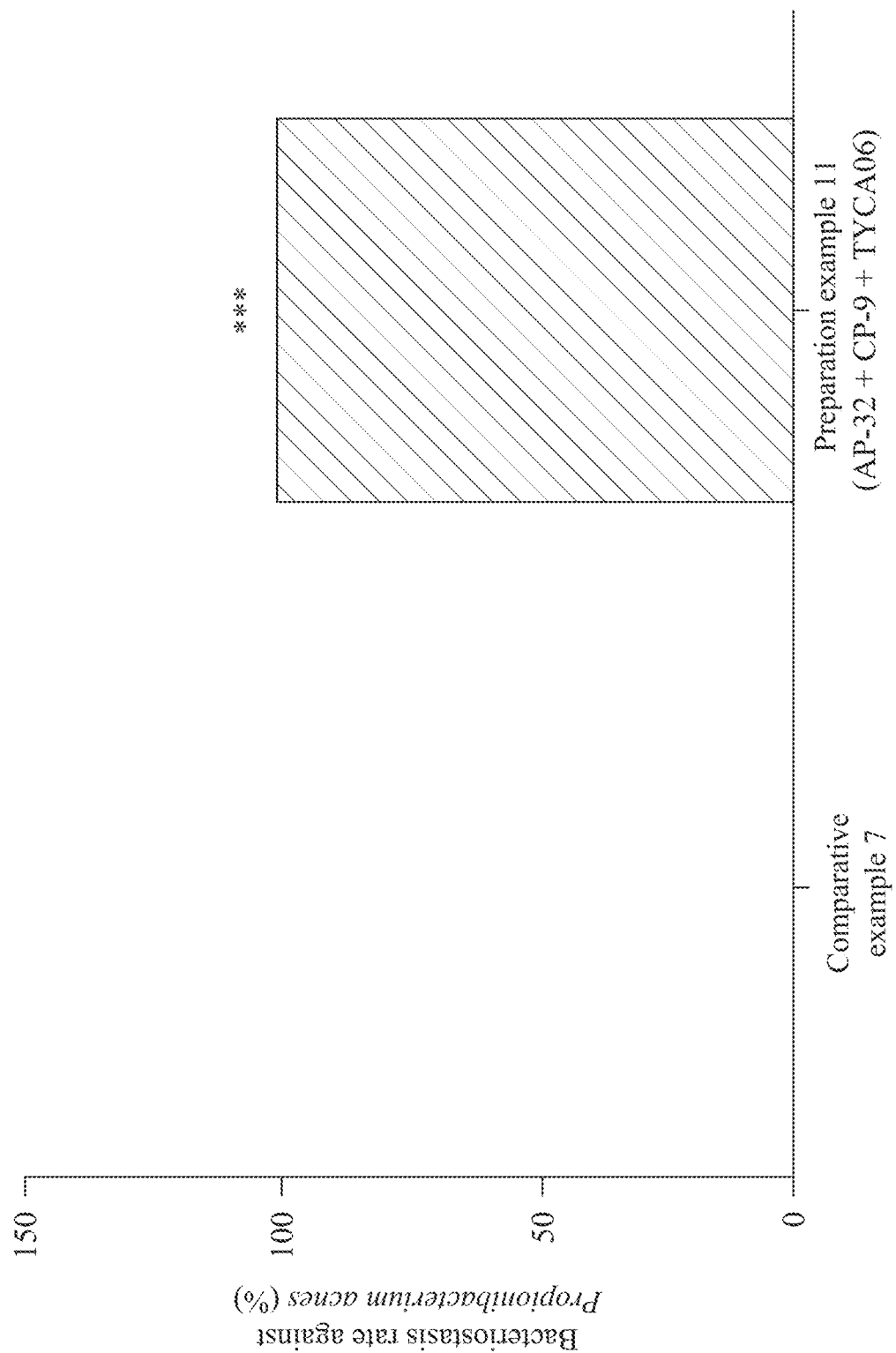
FIG. 6 was a bar chart illustrating the bacteriostasis rate against *Propionibacterium acnes* in accordance with one embodiment of the present invention.

FIG. 6 was a bar chart illustrating the bacteriostasis rate against *Propionibacterium acnes* in accordance with one embodiment of the present invention, in which the horizontal axis represented groups, the longitudinal axis represented bacteriostasis rate, and "*" indicated a statistically significant difference from comparative example 7 using student's t-test statistical analysis (p<0.001). As shown in FIG. 6**, the bacteriostasis rate of preparation example 11 reached 100%, which was significantly greater than that of comparative example 7, showing that the emulsion of preparation example 11 could inhibit *Propionibacterium acnes*.

Example 9. Evaluation of Effect of Fermentation Broth-Containing Gel on Inhibiting Dermatitis The gel of preparation example 11 and the gel of comparative example 7 were respectively administered to acne vulgaris of subjects with acne vulgaris once a day. Then, the conditions of acne vulgaris were observed and recorded on day 0 (before administration), day 3, day 7 and day 14. In addition, on day 0, day 7 and day 14, the inflammation values of acne vulgaris were tested by an intelligent skin analysis system (Yilimei, model ES3100). The percentage of the inflammation value after administration to the inflammation value before administration was taken as an inflammatory index. The aforementioned results were shown in FIG. 7 and FIG. 8.

Figure 7:
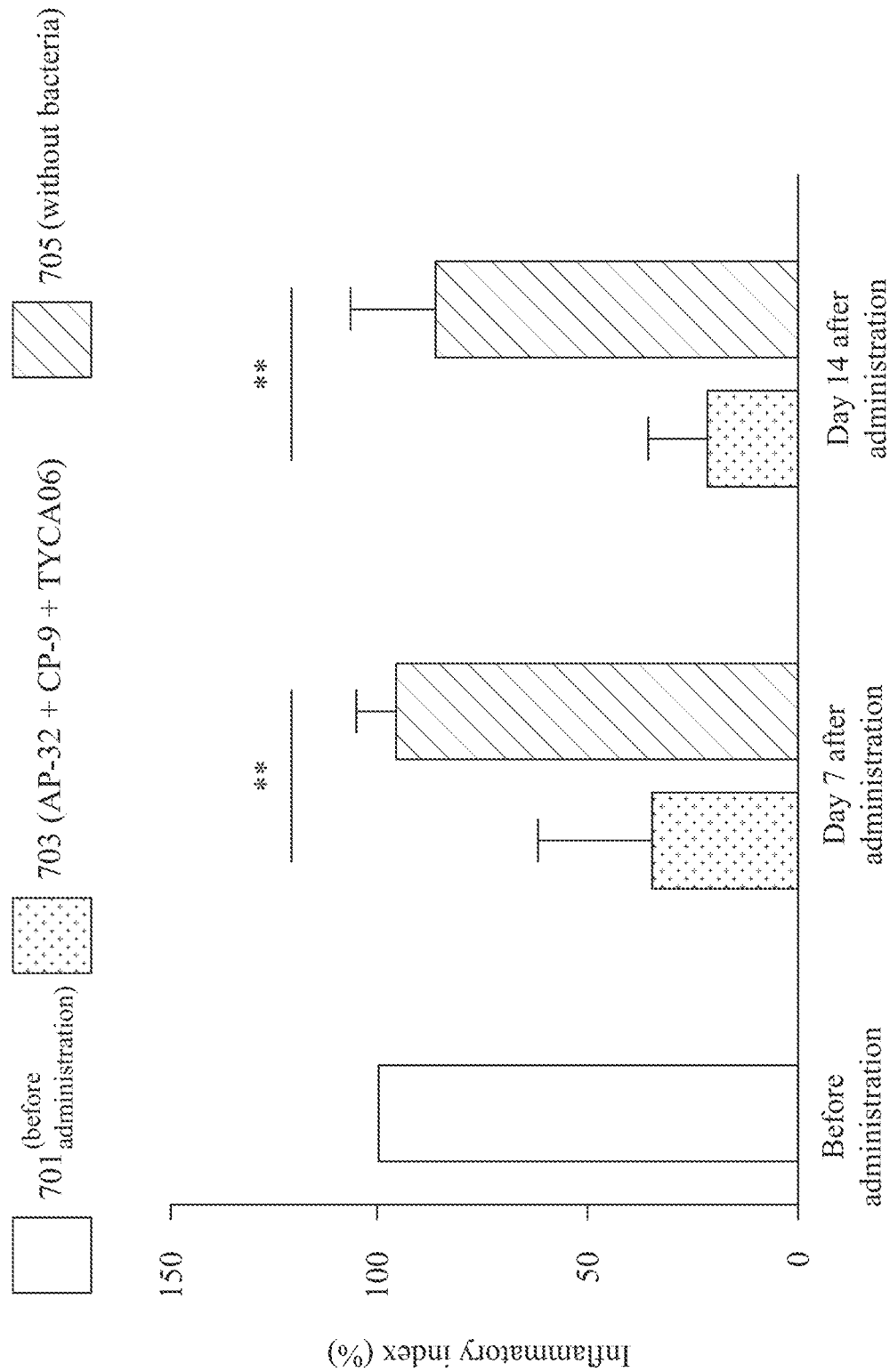
FIG. 7 was a bar chart illustrating the inflammatory index of the affected skin with acne vulgaris after administering the gel in accordance with one embodiment of the present invention.

FIG. 7 was a bar chart illustrating the inflammatory index of the affected skin with acne vulgaris after administering a gel in accordance with one embodiment of the present invention, in which the horizontal axis, from left to right, represented the time before administration, 7 days after administration and 14 days after administration respectively, the vertical axis represented inflammatory index, bar 701, bar 703 and bar 705 represented the state before administration, the state after administering the gel of preparation example 11 and the state after administering the gel of comparative example 7, respectively, and "**" indicated a statistically significant difference between preparation example and comparative example 7 according to student's t-test statistical analysis (p<0.01). As shown in FIG. 7, the inflammatory index before administration (bar 701) was 100%, the inflammatory indexes of preparation example 11 and comparative example 7 were 34% and 95%, respectively, at 7 days after administration, and the inflammatory indexes of preparation example 11 and comparative example 7 were 21% and 86%, respectively, at 14 days after administration. Compared with comparative example 7, the inflammatory index of preparation example 11 was significantly reduced at 7 days or 14 days after administration, indicating that the gel of preparation example 11 could effectively improve inflammation of acne vulgaris.

FIG. 8 was local appearance photos illustrating the affected skin with acne vulgaris at different days after administering a gel in accordance with one embodiment of the present invention. As shown in FIG. 8, the inflammation and swelling of subject B and subject C were remarkably improved at 7 days after the administration of the gel of preparation example 11, and inflammation and swelling of subject A were also remarkably improved at 7 days after the administration of the gel of preparation example 11. However, the skin inflammation and swelling symptoms of subject A, subject B and subject C were not improved at 14 days after the administration of the gel of comparative example 7, showing that the gel of preparation example 11 could effectively eliminate swelling of the affected part of skin with acne vulgaris.

According to the embodiments of the present invention, the topical composition of the present invention are advantageous to include the fermented product of lactic acid bacteria synbiotics instead of the lactic acid bacteria, so that the viability of lactic acid bacteria is not essential, and thus the process can be simplified, as well as such composition is also beneficial for quality control and storage. In addition, the topical composition of the present invention includes a fermented product of lactic acid bacteria synbiotics of a mixture of lactic acid bacteria strains. Compared with a fermented product of lactic acid bacteria synbiotics using a single specific strain, the fermented products of lactic acid bacteria synbiotics of a mixture of specific strains can not only inhibit the growth of skin pathogens more effectively, but also promote cells to secrete anti-inflammatory factors more effectively, thereby having a potential to improve uncomfortable symptoms of skin diseases (such as atopic dermatitis and acne).

It is necessarily supplemented that although specific dosage forms, specific objects, specific delivery means or specific evaluation ways are exemplified for clarifying the topical composition of the present invention and the method of improving skin diseases and dermatitis using the same, it would be apparent to any one of ordinary skilled in the art, that the present invention is not limited to what have mentioned. It is intended that the present invention covers other dosage forms, other objects, other delivery means or other evaluation ways without departing from the spirit and scope of the present invention.

Although the present invention has been disclosed in considerable detail with reference to certain embodiments thereof, other embodiments are possible. Therefore, the spirit and scope of the appended claims should not be limited to the description of the embodiments contained herein.

What is claimed is:

1. A method of inhibiting growth of skin pathogens using a topical composition, wherein the topical composition comprises an effective dose of a fermented product of lactic acid bacteria synbiotics as an active ingredient, the fermented product of lactic acid bacteria synbiotics is obtained by performing a fermenting step with lactic acid bacteria and a sterilizing step on a fermenting substrate, the lactic acid bacteria are consisting of *Lactobacillus salivarius* subsp. *salicinius* AP-32 (accession number CCTCC M 2011127), *Bifidobacterium animalis* subsp. *lactis* CP-9 (accession number CCTCC M 2014588) and *Lactobacillus acidophilus* TYCA06 (accession number CGMCC 15210), the fermenting substrate comprises protein and plant extracts, and the skin pathogens are *Staphylococcus aureus, Propionibacterium acnes* and *Candida albicans*, the plant extracts are extracted from chamomile, wormwood, green tea, calendula or any combination thereof, and the topical composition is applied to an affected skin of a subject in need thereof.

2. The method according to claim 1, wherein the protein comprises animal protein and plant protein, the animal protein comprises milk, milk powder and casein, and the plant protein comprises soybeans and soybean products.

3. The method according to claim 1, wherein the fermented product of lactic acid bacteria synbiotics comprises a fermentation broth with an effective dose of 2 weight % (wt %) to 30 wt %.

4. The method according to claim 1, wherein the fermented product of lactic acid bacteria synbiotics comprises a dried fermented product with an effective dose of 0.4 wt % to 6 wt %.

5. The method according to claim 1, wherein the topical composition further comprises pharmaceutically or cosmetically available carriers, excipients, diluents, adjuvants, and/or additives.

6. The method according to claim 1, wherein the topical composition further comprises a gelling agent, a preservative, a plant oil, a humectant.

7. The method according to claim 1, wherein a dosage form of the topical composition is a tablet, a capsule, a powder, a cream, a spray, a gel, a solution, a pulvis, or a lotion.

* * * * *